(12) United States Patent
Oishi

(10) Patent No.: US 7,563,376 B2
(45) Date of Patent: *Jul. 21, 2009

(54) PLASMA PURIFICATION MEMBRANE AND PLASMA PURIFICATION SYSTEM

(75) Inventor: Teruhiko Oishi, Fuji (JP)

(73) Assignee: Asahi Kasei Kuraray Medical Co., Ltd., Tokyo (JP)

( * ) Notice: Subject to any disclaimer, the term of this patent is extended or adjusted under 35 U.S.C. 154(b) by 396 days.

This patent is subject to a terminal disclaimer.

(21) Appl. No.: 10/527,802

(22) PCT Filed: Sep. 12, 2003

(86) PCT No.: PCT/JP03/11715

§ 371 (c)(1),
(2), (4) Date: Sep. 22, 2005

(87) PCT Pub. No.: WO2004/024216

PCT Pub. Date: Mar. 25, 2004

(65) Prior Publication Data

US 2006/0108288 A1    May 25, 2006

(30) Foreign Application Priority Data

Sep. 12, 2002  (JP)  ............................. 2002-267266
Sep. 12, 2002  (JP)  ............................. 2002-267267

(51) Int. Cl.
  *B01D 33/00*  (2006.01)
  *B01D 11/00*  (2006.01)
  *B29C 65/00*  (2006.01)
  *B29C 47/00*  (2006.01)

(52) U.S. Cl. ............. 210/645; 210/500.42; 210/500.23; 210/500.41; 210/195.2; 264/176.1; 264/177.14; 264/41

(58) Field of Classification Search ............ 210/599.27, 210/500.41, 500.42, 500.23, 321.71, 645, 210/500.27, 195.2; 264/41, 177.26, 177.14, 264/176.1, DIG. 48, 177.1, DIG. 486
See application file for complete search history.

(56) References Cited

U.S. PATENT DOCUMENTS

| 3,871,950 | A | * | 3/1975 | Hashino et al. | ............. 428/398 |
| 4,789,733 | A | * | 12/1988 | Winkelman | ................. 530/383 |
| 4,882,223 | A | * | 11/1989 | Aptel et al. | ................. 428/398 |
| 4,906,375 | A | * | 3/1990 | Heilmann | ............. 210/500.23 |
| 5,232,597 | A | * | 8/1993 | Eguchi | ................. 210/500.23 |

(Continued)

FOREIGN PATENT DOCUMENTS

| EP | 0 168 783 | 1/1986 |
| EP | 0 264 931 | 4/1988 |
| EP | 0 882 494 | 12/1998 |

(Continued)

*Primary Examiner*—Ana M Fortuna
(74) *Attorney, Agent, or Firm*—Young & Thompson

(57) ABSTRACT

A plasma purification membrane and a plasma purification system for treating diseases. The above plasma purification membrane is a hollow fiber plasma purification membrane being made of a hydrophobic polymer and a hydrophilic polymer and having a sponge-like structure wherein the pore size is continuously decreased from the outer surface of the membrane toward the inner surface thereof, characterized in that the break strength of the membrane is 50 kgf/cm$^2$ or more and, in the case of the inner pressure filtration of bovine plasma, the total protein permeability is 50% or more while the immunoglobulin (IgM) permeability is 90% or less.

24 Claims, 3 Drawing Sheets

U.S. PATENT DOCUMENTS

| | | | |
|---|---|---|---|
| 5,340,480 A * | 8/1994 | Kawata et al. | 210/500.23 |
| 5,683,584 A * | 11/1997 | Wenthold et al. | 210/500.23 |
| 5,762,798 A * | 6/1998 | Wenthold et al. | 210/500.23 |
| 5,938,929 A * | 8/1999 | Shimagaki et al. | 210/645 |
| 6,074,718 A * | 6/2000 | Puglia et al. | 428/36.5 |
| 6,165,363 A * | 12/2000 | Oishi et al. | 210/500.23 |
| 7,087,168 B2 * | 8/2006 | Oishi et al. | 210/500.23 |
| 7,153,473 B2 * | 12/2006 | Ericson et al. | 422/44 |

FOREIGN PATENT DOCUMENTS

| | | |
|---|---|---|
| JP | 4-3985 | 1/1992 |
| JP | 3281364 | 5/2002 |
| WO | WO 86/02575 | 5/1986 |
| WO | WO 96/14890 | 5/1996 |

* cited by examiner

PLASMA PURIFICATION MEMBRANE AND PLASMA PURIFICATION SYSTEM

TECHNICAL FIELD

The present invention relates to a plasma purification membrane for plasma purification using inside-out filtration which is rarely clogged and has high strength, and a method for producing the same. The present invention also relates to a plasma purification system and a method for treating diseases using the plasma purification membrane.

BACKGROUND ART

A hollow fiber membrane has been widely used for industrial applications such as microfiltration and ultrafiltration. As to the material used in the membrane, polyethylene, cellulose acetate, polysulfone, polyvinylidene fluoride, polycarbonate, polyacrylonitrile, or the like has been used. A conventional hollow fiber membrane formed of such a material has been developed mainly aiming at improving filtration performance. Therefore, as a conventional hollow fiber membrane exhibits low breaking stress and elongation at break, the hollow fiber membrane breaks due to a rapid temperature change or a pressure fluctuation when shifting to backwash.

Various attempts have been made to solve this problem. As suggested by the invention disclosed in Japanese Patent Application Laid-open No. 59-228016, a method wherein the polymer density of the entire hollow fiber membrane is increased by increasing the polymer concentration in the membrane-forming solution may be generally considered. This method improves the strength of the membrane, but decreases the pore size of the membrane and considerably decreases the water permeability of the membrane. As a result, a hollow fiber membrane having well-balanced strength and water permeability has not as yet been obtained.

The pore size of the membrane is generally increased in order to improve water permeability of the membrane. However, an increase in the pore size generally decreases the fractionation (cutoff) performance and the strength of the membrane.

As described above, a high-performance hollow fiber membrane having well-balanced strength, water permeability, and fractionation performance has not been obtained by a conventional technology. For example, Japanese Patent Application Laid-open No. 04-260424 proposes a method for producing a membrane having high strength and excellent water permeability. However, since the membrane obtained by this method has a large pore size, the water permeability and fractionation performance is not well-balanced.

Japanese Patent Application Laid-open No. 02-102722 discloses a hollow fiber microfiltration membrane in which the pore size is continuously decreased from the outer surface toward the inside of the membrane, is minimized inside the membrane, is continuously increased again toward the inner surface, and is open on the inner surface. However, when filtering liquid or the like from the side of the hollow section (inner surface side) of a membrane having this structure, filtration cannot be stably performed for a long period of time due to the occurrence of rapid clogging.

Japanese Patent Application Laid-open No. 58-155865 discloses a hollow fiber membrane having a dense layer on at least one surface side of the hollow fiber membrane and a porous layer inside the hollow fiber membrane. Japanese Patent Application Laid-open No. 58-155865 discloses a hollow fiber membrane made of a vinyl alcohol polymer, but does not disclose a membrane material comprising a hydrophobic polymer and a hydrophilic polymer. If the hydrophilic polymer is included in the hydrophobic polymer, the molecular chains of the hydrophobic polymer become poorly entangled with each other, whereby a high strength may not be obtained. Moreover, since the hollow fiber membrane made of a vinyl alcohol polymer disclosed in Japanese Patent Application Laid-open No. 58-155865 has a structure in which the dense layer is formed on the outer surface of the membrane, filtration cannot be stably performed for a long period of time due to the occurrence of clogging when a liquid or the like is filtered from the side of the hollow section (inner surface side) of the membrane.

The applicant of the present invention has provided a hollow fiber membrane comprising a hydrophobic polymer and a hydrophilic polymer and having a sponge structure in which the pore size is continuously decreased from the outer surface to the inner surface of the membrane. However, this membrane can be merely used for blood dialysis or ultrafiltration which does not substantially cause albumin to pass therethrough, and is not suitable for plasma purification (Japanese Patent Application Laid-open No. 11-309355, Japanese Patent No. 3281364, and Japanese Patent No. 3281363).

As described above, a hollow fiber membrane for plasma purification which is well-balanced, exhibits a desired strength, water permeability, and fractionation performance, and which rarely clogs even when filtering liquid from the side of the hollow section (inner surface side), has not yet been provided.

DISCLOSURE OF THE INVENTION

Figure 1:
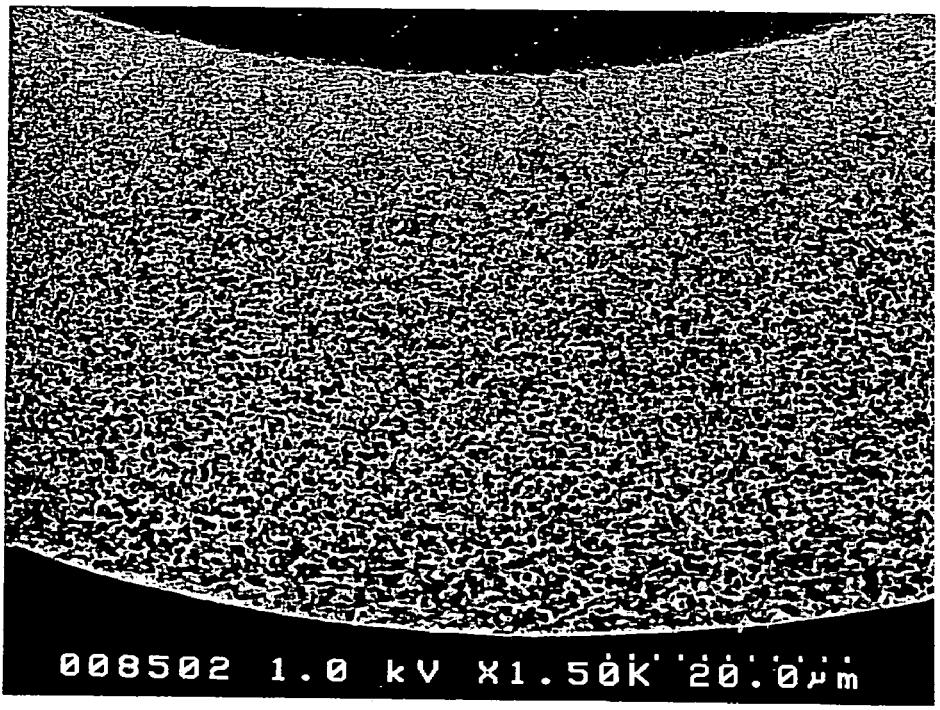
FIG. 1 is an electron micrograph of the cross section perpendicular to the longitudinal direction of a hollow fiber membrane of the present invention (magnification: ×1,500).

An objective of the present invention is to provide a plasma purification membrane which rarely clogs, has high strength, and exhibits excellent water permeability and fractionation performance in plasma purification using inside-out filtration. Another objective of the present invention is to provide a plasma purification system and a method for treating disease using such a plasma purification membrane.

As described above, a plasma purification membrane which rarely clogs and exhibits excellent protein separation properties when filtering liquid or the like from the side of the hollow section of the membrane (hereinafter may be called "inside-out filtration") has not yet been provided. This is because it is impossible to form a pore with a large pore size (pore size in microfiltration membrane region) which allows plasma protein to pass therethrough in the inner surface of the membrane having a gradient structure, in which the pore size is continuously decreased from the outer surface to the inner surface of the membrane, while maintaining the strength of the membrane.

The present inventor has conducted extensive studies to achieve the above objectives while 1) forming a gradient structure in which the pore size is continuously decreased from the outer surface to the inner surface of the membrane in order to prevent clogging, and 2) increasing hydrophilicity of the inner surface of the membrane with which a liquid to be filtered comes into contact so that protein or the like does not undergo hydrophobic adsorption. As a result, the present inventor has found that a desired membrane can be obtained by using a specific production method. This finding has led to the completion of the present invention.

The above and other objectives, features, and advantages of the present invention will become apparent from the following detailed description and the appended claims.

According to the present invention, a plasma purification membrane which rarely clogs, has high strength, and exhibits excellent water permeability and fractionation performance in plasma purification using inside-out filtration can be provided.

The basic features and preferred embodiments of the present invention are given below in order to facilitate better understanding of the present invention.

(1) A hollow fiber plasma purification membrane, comprising a hydrophobic polymer and a hydrophilic polymer, having a sponge structure in which a pore size is continuously decreased from an outer surface to an inner surface of the membrane, and having a breaking stress of 50 kgf/cm$^2$ or more, and a total protein permeability of 50% or more and an immunoglobulin (IgM) permeability of 90% or less when subjecting bovine plasma to inside-out filtration.

(2) The hollow fiber plasma purification membrane according to (1) above, the membrane has circular or elliptical pores having an average pore size of 1 μm or more on the outer surface of the membrane.

(3) The hollow fiber plasma purification membrane according to (1) or (2), wherein porosity of the outer surface of the membrane is 10% or more.

(4) The hollow fiber plasma purification membrane according to any one of (1) to (3), wherein the membrane has a ratio of thickness to internal diameter of 0.15 to 0.4.

(5) The hollow fiber plasma purification membrane according to any one of (1) to (4), wherein the membrane has an external diameter of 400 μm or less.

(6) The hollow fiber plasma purification membrane according to any one of (1) to (5), wherein the membrane comprises an aromatic polysulfone and polyvinylpyrrolidone, and a polyvinylpyrrolidone concentration on the inner surface of the membrane is 20 to 45 wt %.

(7) The hollow fiber plasma purification membrane according to (6), wherein the polyvinylpyrrolidone has a weight average molecular weight of 900,000 or more.

(8) The hollow fiber plasma purification membrane according to any one of (1) to (7), wherein the membrane comprises water-insoluble polyvinylpyrrolidone.

(9) The hollow fiber plasma purification membrane according to any one of (1) to (8), wherein the membrane is used to treat a patient suffering from age-related macular degeneration.

(10) The hollow fiber plasma purification membrane according to any one of (1) to (8), wherein the membrane is used to treat a patient suffering from hyperlipidemia.

(11) A method for producing a hollow fiber plasma purification membrane comprising a hydrophobic polymer and a hydrophilic polymer, having a sponge structure in which a pore size is continuously decreased from an outer surface to an inner surface of the membrane, and having a breaking stress of 50 kgf/cm$^2$ or more, and a total protein permeability of 50% or more and an immunoglobulin (IgM) permeability of 90% or less when subjecting bovine plasma to inside-out filtration, comprising the steps of: discharging a membrane-forming solution and an internal solution from a double annular nozzle, passing the discharged mixture through an air gap, and coagulating the resulting mixture in a coagulation bath;

the method further characterized in that:

a) the membrane-forming solution comprises a hydrophobic polymer, a solvent for the hydrophobic polymer, and a hydrophilic polymer, and has a ratio of the hydrophilic polymer to the hydrophobic polymer of 27 to 60 wt %;

b) the internal solution comprises water and at least one solvent, and has a water content of 40 to 55 wt %;

c) the membrane-forming solution has a temperature of 50° C. or more at the nozzle;

d) the coagulation bath has a temperature of 90 to 100° C.; and e) a ratio of the air gap to a spinning speed is 0.01 to 0.1 m/(m/min).

(12) The method for producing a hollow fiber plasma purification membrane according to (11), further comprising the step of applying radiation to the membrane.

(13) The method for producing a hollow fiber plasma purification membrane according to (11) or (12), wherein the hydrophobic polymer is a polysulfone polymer.

(14) The method for producing a hollow fiber plasma purification membrane according to any one of (11) to (13), wherein the solvent for the hydrophobic polymer is N-methyl-2-pyrrolidone.

(15) The method for producing a hollow fiber plasma purification membrane according to any one of (11) to (14), wherein the spinning speed is 60 m/min or more.

(16) A plasma purification system, comprising a plasma separator including a separation membrane which separates blood into blood cell components and plasma components; a plasma component separator including a separation membrane which separates the separated plasma components into pathogenic substances and plasma components from which the pathogenic substances are removed or reduced; first mixing means for mixing the plasma components from which the pathogenic substances are removed or reduced with a replenishment solution; and second mixing means for further mixing the plasma components subjected to the first mixing means with the blood cell components separated by the plasma separator; wherein the separation membrane included in the plasma component separator is the membrane according to any one of (1) to (10).

(17) The plasma purification system according to (16), further comprising means for heating plasma upstream of the second mixing means for mixing the plasma components with the blood cell components.

(18) The plasma purification system according to (16) or (17), comprising means for heating or cooling plasma downstream of the plasma separator and upstream of the plasma component separator.

(19) The plasma purification system according to any one of (16) to (18), wherein an amount of discharge liquid including the pathogenic substances discharged from the plasma component separator is equal to an amount of the replenishment solution.

(20) The plasma purification system according to any one of (16) to (19), which is controlled so that an amount of the plasma supplied from the plasma separator to the plasma component separator is equal to an amount of the plasma returned to the second mixing means.

(21) The plasma purification system according to any one of (16) to (20), further comprising means for detecting bubbles in the blood downstream of the second mixing means and upstream of a blood outlet.

(22) A plasma purification method, comprising using the plasma purification system according to any one of (16) to (21).

(23) A method for treating disease, comprising treating blood of a living body using the plasma purification system according to any one of (16) to (21).

(24) A method for treating a patient suffering from age-related macular degeneration, comprising using the plasma purification system according to any one of (16) to (21).

(25) A method for treating a patient suffering from hyperlipidemia, comprising using the plasma purification system according to any one of (16) to (21).

The configuration of the hollow fiber blood purification membrane (hereinafter may be simply called "membrane" or "hollow fiber membrane") of the present invention is described below.

In the present invention, plasma purification means separating components in plasma. For example, plasma purification means causing useful proteins in plasma such as albumin and γ-globulin to permeate, and removing unnecessary proteins and lipids. However, since the removal target components, the fractionation (cutoff) molecular weight, and the like differ depending on the type of disease, the plasma purification in the present invention broadly includes separating the components in plasma.

The hollow fiber membrane of the present invention has a structure in which the membrane is integrally and continuously formed from one surface to the other surface, such as from the inner surface to the outer surface of the membrane. The inside of the membrane from one surface to the other surface of the membrane has a mesh structure having a mesh (pore) size of 10 μm or less, and does not include a polymer deficiency (large pore or void) with a pore size of more than 10 μm. In the present invention, this structure is referred to as a sponge structure.

The pore of the mesh structure inside the membrane has a gradient structure in which the pore size is continuously decreased from the outer surface to the inner surface (or inner surface region) of the membrane in the cross section perpendicular to the longitudinal direction of the membrane. Specifically, assuming some cylindrical surfaces are concentric to the center axis extending in the longitudinal direction of the hollow fiber membrane, the average pore size of the pores in each cylindrical surface is continuously decreased from the outer surface to the inner surface (or inner surface region) of the membrane. This structure is indispensable for ensuring sharp fractionation performance (excellent protein separation properties) when subjecting plasma to inside-out filtration.

A typical example of the membrane of the present invention is described below in more detail with reference to the drawings.

Figure 2:
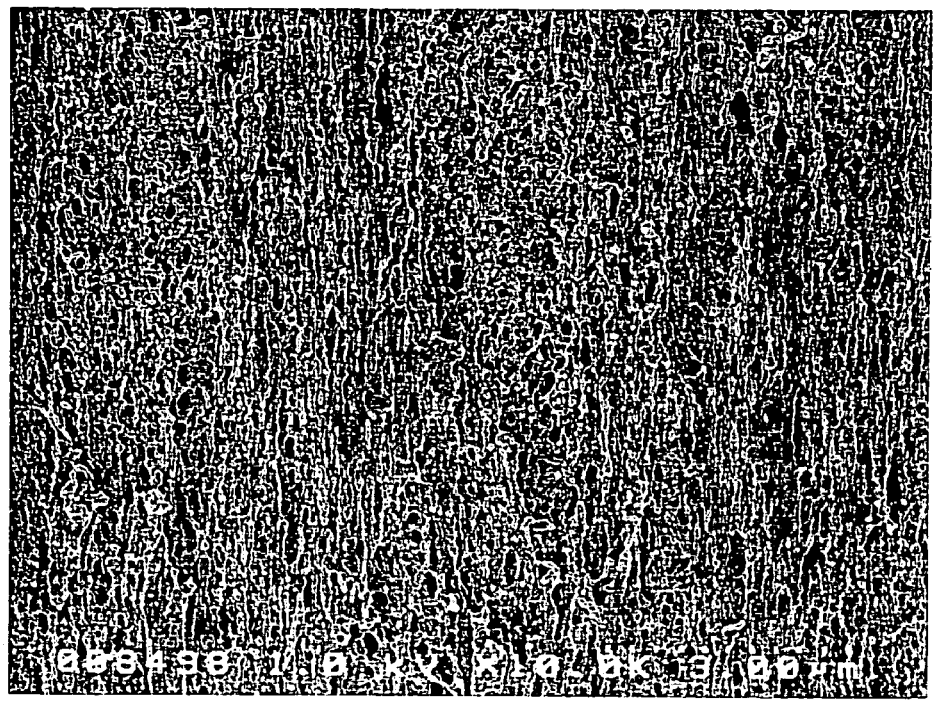
FIG. 2 is an electron micrograph of the inner surface of a membrane of the present invention (magnification: ×10,000).
Figure 3:
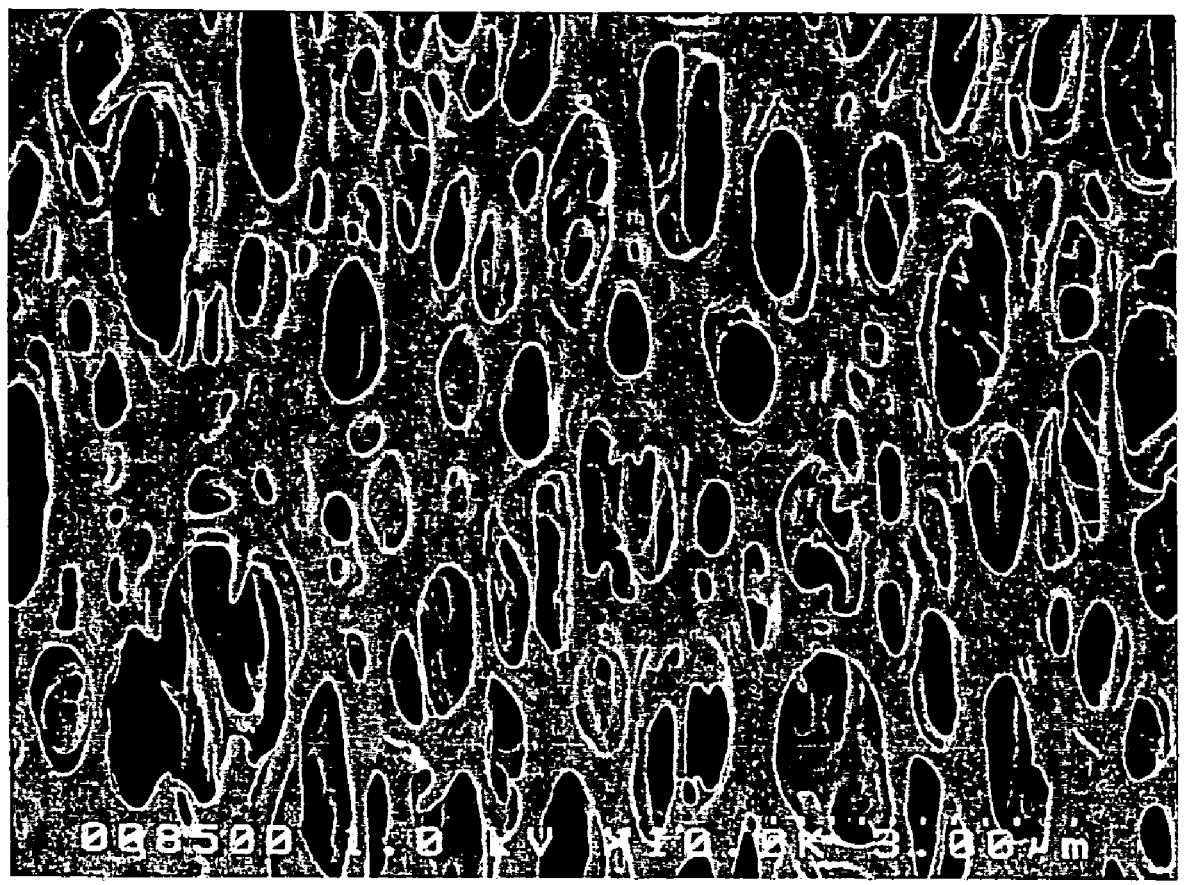
FIG. 3 is an electron micrograph of the outer surface of a membrane of the present invention (magnification: ×10,000).

FIG. 1 is an electron micrograph of a cross section (part) perpendicular to the longitudinal direction of the hollow fiber membrane. FIG. 2 is an electron micrograph showing the state of the inner surface of the membrane, and FIG. 3 is an electron micrograph showing the state of the outer surface of the membrane.

As shown in FIG. 1, the membrane has a gradient structure in which the average pore size is gradually and continuously decreased to the inner surface of the membrane, that is, a mesh structure having a pore size anisotropy. The inner surface of the membrane has a dense structure. However, the membrane of the present invention does not have a definite skin layer as known in the prior art. FIG. 2 shows the state of the dense inner surface. On the other hand, circular or elliptical pores are observed on the outer surface as shown in FIG. 3.

It is preferable that the pore openings on the inner surface of the membrane be circular, elliptical, mesh, or slit-shaped. It is preferable that the pore openings on the outer surface be circular or elliptical.

The average pore size of the pores opening on the outer surface of the membrane is 1 μm or more, and preferably 2 μm or more, but 30 μm or less. If the pore size is less than 1 μm, a molding failure may unpreferably occur due to adhesion between membranes.

The porosity of the outer surface is also important in order to prevent adhesion between membranes. The porosity used in the present invention may be determined by image-analyzing an electron micrograph of the outer surface of the dried membrane, and converting the image-analyzed results into numerical values. The porosity used in the present invention is defined as the percentage of the sum of the pore areas in the porous section with respect to the area of the photographed image, and is represented by the following equation (1). Pores having a size of 10 pixels or less were excluded from the calculation as noise.

$$\text{Porosity (\%)} = (\text{sum of pore areas in porous section}/\text{area of photographed image}) \times 100 \quad (1)$$

The porosity considerably affects adhesion between membranes. If the porosity is small, adhesion occurs due to an increase in the contact area between adjacent membranes. In worst cases, the entire bundle adheres in the shape of a rod.

Therefore, the porosity must be 10% or more.

However, if the porosity is unnecessarily increased, flexibility of the membrane in the longitudinal direction, that is, the elastic strength is decreased, whereby a considerable molding failure frequently occurs during molding due to membrane flow and movement at the adhesion part. Therefore, it is preferable that the porosity must be 60% or less in order not to impair the elastic strength.

The shape, size, and the like of the pores opening on the surface of the membrane may be observed and measured by using an electron microscope.

An average pore size D of the pores opening on the inner surface or the outer surface is a value represented by the following equation (2).

$$D = [\{(D_i^2)^2 + \ldots + (D_n^2)^2\}/\{D_i^2 + \ldots D_n^2\}]^{1/2} \quad (2)$$

In the equation (2), D indicates the average pore size, Di indicates the measured diameter of the i-th pore, and Dn indicates the measured diameter of the n-th pore. The measured diameter Di or Dn is indicated by the diameter of the pore when the pore is almost circular, and is indicated by the diameter of the circle having the same area as the area of the pore when the pore is not circular.

The membrane of the present invention has a total protein permeability of 50% or more, and preferably 80% or more when subjecting bovine plasma to inside-out filtration. If the total protein permeability is less than 50%, since considerable amounts of albumin (Alb) and γ-globulin (IgG) (molecular weight: about 160,000) which are very needed by the human body are lost, it becomes difficult to use the membrane for treating a patient whose physical strength has decreased.

The membrane of the present invention has a permeability of immunoglobulin (IgM) (molecular weight: about 950,000) of 90% or less when subjecting bovine plasma to inside-out filtration. While albumin and γ-globulin are proteins very needed by the human body, it is necessary to remove high-molecular-weight proteins, such as immunoglobulin, or lipids depending on the type of disease. If the permeability exceeds 90%, the membrane may not be effective against diseases such as hyperlipidemia.

The membrane of the present invention has a breaking stress of 50 kgf/cm² or more, and preferably 60 kgf/cm² or more, even though the membrane has a gradient structure, in which the pore size is continuously decreased from the outer surface to the inner surface of the membrane, and includes a pore with a large pore size which allows plasma protein to pass through the inner surface of the membrane. If the breaking stress of the membrane is less than 50 kgf/cm², a considerable leakage or the like occurs. The breaking stress used in the present invention may be determined by dividing the breaking load (kgf) applied to one hollow fiber membrane by the cross-sectional area (cm²) of the membrane before applying a load.

The hollow fiber membrane of the present invention includes a hydrophobic polymer and a hydrophilic polymer.

As examples of the hydrophobic polymer, a polysulfone polymer, a polyethylene polymer, a polypropylene polymer, a polyvinylidene fluoride polymer, and the like can be given. The polysulfone polymer and the polyvinylidene fluoride polymer are preferable from the viewpoint of forming the membrane using a wet process. Of these, the aromatic polysulfone is most preferably used, since the aromatic polysulfone has heat stability, acid resistance, and alkali resistance, and improves blood compatibility by adding the hydrophilic polymer to the membrane-forming solution and forming a membrane using the resulting solution. As the aromatic polysulfone, a bisphenol A polysulfone is particularly preferably used.

The hydrophilic polymer is not particularly limited insofar as the polymer may swell in water but is not dissolved in water. As examples of such a polymer, polymers including a substituent such as a sulfonic acid group, a carboxyl group, a carbonyl group, an amino group, an amide group, a cyano group, a hydroxyl group, a methoxy group, a phosphoric acid group, a polyoxyethylene group in which the number of repeating units is about 1 to 40, an imino group, an imide group, an imino ether group, a pyridine group, a pyrrolidone group, an imidazole group, and a quaternary ammonium group, either individually or in combination of two or more, can be given.

In order to form a membrane using a wet process, a polymer which is miscible with a solvent and is not miscible with the hydrophobic polymer may be used as the hydrophilic polymer. When the hydrophobic polymer which constitutes the hollow fiber membrane is an aromatic polysulfone, polyvinylpyrrolidone is most preferable as the hydrophilic polymer.

As described above, it is most preferable that the membrane of the present invention comprises the aromatic polysulfone and polyvinylpyrrolidone. Since the plasma purification membrane of the present invention is used for inside-out filtration, it is preferable that the concentration of polyvinylpyrrolidone on the inner surface of the membrane with which plasma comes into contact be 20 to 45 wt %. The plasma protein easily undergoes hydrophobic adsorption. Therefore, the important factor for preventing clogging during inside-out filtration is the hydrophilicity of the inner surface of the membrane with which the plasma comes into contact. In the polysulfone membrane including polyvinylpyrrolidone (hereinafter may be abbreviated as "PVP"), the PVP-concentration on the inner surface of the membrane is important. If the PVP concentration on the inner surface of the membrane is too low, the inner surface of the membrane exhibits hydrophobicity, whereby the plasma protein is easily absorbed on the inner surface of the membrane. If the PVP concentration on the inner surface of the membrane is too high, the amount of PVP eluted into the plasma is increased, and undesirable results may result. Therefore, the PVP concentration when subjecting plasma to inside-out filtration is 20 to 45 wt %, and preferably 25 to 40 wt %.

As the polysulfone polymer used in the present invention, a polymer including a repeating unit represented by the following formula (3) or (4) can be given. In the formula, Ar represents a di-substituted (para position) phenyl group, and the degree of polymerization and the molecular weight are not particularly limited.

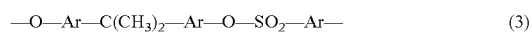

—O—Ar—C(CH₃)₂—Ar—O—SO₂—Ar— (3)

—O—Ar—SO₂—Ar— (4)

Since polyvinylpyrrolidone having a higher molecular weight exerts a higher hydrophilic effect on the membrane, a sufficient effect can be obtained with a smaller amount of addition. Therefore, polyvinylpyrrolidone having a weight average molecular weight of 900,000 or more is used in the present invention. In order to provide the hydrophilic effect to the membrane using polyvinylpyrrolidone having a weight average molecular weight of less than 900,000, a large amount of polyvinylpyrrolidone must be allowed to remain in the membrane. This causes the amount of substance eluted from the membrane to be increased. If the amount of polyvinylpyrrolidone having a weight average molecular weight of less than 900,000 remaining in the membrane is decreased in order to decrease the amount of substance eluted from the membrane, the hydrophilic effect becomes insufficient. If polyvinylpyrrolidone having a weight average molecular weight of 900,000 or more is not used, hydrophilicity becomes insufficient in the thick section of the membrane, whereby plasma protein which has passed through the inner surface region of the membrane adheres in the thick section. As a result, excellent separation properties cannot be obtained.

The PVP concentration on the inner surface of the membrane is determined by X-ray photoelectron spectroscopy (XPS). Specifically, the inner surface of the membrane is subjected to XPS measurement by placing a specimen on a double-sided tape, cutting the specimen in the fiber axial direction using a cutter, spreading the cut specimen so that the inside of the membrane is the upper side, and measuring the PVP concentration using a conventional method. Specifically, the PVP concentration used herein refers to the concentration determined from the surface nitrogen concentration (nitrogen atom concentration) and the surface sulfur concentration (sulfur atom concentration) obtained from the area intensity of C1s, O1s, N1s, and S2p spectra using the relative sensitivity coefficient peculiar to the measurement device. When the polysulfone polymer has a structure shown by the formula (3), the PVP concentration may be calculated using the following equation (5).

$$\text{PVP concentration (wt \%)} = C_1 M_1 \times 100 / (C_1 M_1 + C_2 M_2) \quad (5)$$

Where,
$C_1$: nitrogen atom concentration (%)
$C_2$: sulfur atom concentration (%)
$M_1$: molecular weight of PVP repeating unit (111)
$M_2$: molecular weight of polysulfone polymer repeating unit (442)

The membrane of the present invention includes water-insoluble PVP. If the entire PVP in the membrane is water-soluble, the amount of substance eluted from the membrane is unpreferably increased. If the entire PVP is water-insoluble, excellent protein separation performance is not obtained since the inner surface (or inner surface region) of the membrane exhibits poor swelling properties during plasma filtration. The membrane of the present invention exhibits excellent membrane performance since the membrane includes water-insoluble PVP in an appropriate amount.

A method for producing the hollow fiber membrane of the present invention is described below.

The hollow fiber membrane of the present invention may be produced by using a method for producing a hollow fiber membrane, comprising the steps of: discharging a membrane-forming solution and an internal solution from a double annular nozzle, passing the discharged mixture through an air gap, and coagulating the resulting mixture in a coagulation bath; the method characterized in that:

a) the membrane-forming solution comprises a hydrophobic polymer, a solvent for the hydrophobic polymer, and a hydrophilic polymer, and has a ratio of hydrophilic polymer to hydrophobic polymer of 27 to 60 wt %;

b) the internal solution comprises water and at least one solvent, and has a water content of 40 to 55 wt %;

c) the membrane-forming solution has a temperature of 50° C. or more at the nozzle;

d) the coagulation bath has a temperature of 90 to 100° C.; and e) a ratio of the air gap to spinning speed is 0.01 to 0.1 m/(m/min).

The hollow fiber membrane of the present invention is produced by discharging a membrane-forming solution which essentially consists of a hydrophobic polymer, a solvent for the hydrophobic polymer, and a hydrophilic polymer, from a double annular nozzle together with an internal solution comprising an aqueous solution of a good solvent for the polymer at a specific concentration, causing the discharged mixture to pass through an air gap, and causing the resulting mixture to coagulate in a coagulation bath.

As to the solvent for the polymer, N-methyl-2-pyrrolidone, N,N-dimethylformamide, N,N-dimethylacetamide, and the like can be used. When the hydrophobic polymer is the polysulfone polymer, N-methyl-2-pyrrolidone (hereinafter may be abbreviated as "NMP") is preferable. NMP is a solvent having the highest dissolution capability for the polysulfone polymer. For example, NMP has a dissolution capability about 1.5 times that of N,N-dimethylacetamide, which is another good solvent, at room temperature. In a gradient structure in which the pore size is continuously decreased from the outer surface to the inner surface of the membrane, in order to form a pore with a large pore size which allows plasma protein to pass therethrough in the inner surface of the membrane, it is necessary to increase the period of time from the beginning of liquid-liquid phase separation induced by the non-solvent in the internal solution to the completion of the phase separation (coagulation) (particle growth time). The polysulfone polymer allows the particle growth time to be increased by using NMP having an extremely high dissolution capability in comparison with the case of using another solvent. Since NMP is the best solvent for the polysulfone polymer, the molecular chains of the polysulfone polymer in the membrane forming solution are well entangled, whereby a membrane having high strength can be obtained. Therefore, when using the polysulfone polymer as the hydrophobic polymer, the membrane of the present invention is scarcely obtained by using a solvent other than NMP.

The membrane-forming solution essentially consists of the hydrophobic polymer, a specific hydrophilic polymer such as polyvinylpyrrolidone, and a specific solvent such as N-methyl-2-pyrrolidone. If other additives, for example, water, a metal salt and the like known in the art as conventional additives, are added to the membrane-forming solution, it is difficult to obtain the membrane of the present invention.

The hydrophobic polymer concentration in the membrane-forming solution used in the present invention is not particularly limited insofar as a membrane can be produced from the membrane-forming solution and the resulting membrane has required membrane properties. The hydrophobic-polymer concentration is 10 to 35 wt %, and preferably 10 to 30 wt %. In order to achieve high water permeability and high fractionation (cutoff) molecular weight, the polymer concentration is preferably as low as 10 to 25 wt %.

The amount of hydrophilic polymer in the membrane-forming solution is also important. The mixing ratio of the hydrophilic polymer to the hydrophobic polymer is 27 to 60 wt %, and preferably 30 to 60 wt %. If the mixing ratio of the hydrophilic polymer to the hydrophobic polymer is less than 27 wt %, protein permeability may be decreased when subjecting bovine plasma to inside-out filtration. If the mixing ratio exceeds 60 wt %, the viscosity of the membrane-forming solution is increased, whereby spinnability tends to become poor during membrane formation.

The temperature of the membrane-forming solution is important, and is 50° C. or more, and preferably 60 to 100° C. when discharging the solution from the nozzle. If the temperature is less than 50° C., spinnability tends to become poor during membrane formation.

The internal solution is used for forming the hollow section of the hollow fiber membrane, and comprises water and at least one good solvent for the hydrophobic polymer. The water content is preferably 40 to 55 wt %. If the water content is less than 40 wt %, spinnability is poor during membrane formation. If the water content exceeds 55 wt %, the protein permeability may be decreased when subjecting bovine plasma to inside-out filtration. The air gap means the distance between the nozzle and the coagulation bath. The ratio of the air gap (m) to the spinning speed (m/min) is very important in order to obtain the membrane of the present invention. This is because the membrane structure of the present invention can be obtained on the condition that phase separation from the inner surface region to the outer surface region of the membrane-forming solution is induced due to the contact of the membrane-forming solution with the non-solvent component in the internal solution, and that the phase separation from the inner surface region to the outer surface region of the membrane has been completed before the membrane-forming solution enters into the coagulation bath.

The ratio of the air gap to the spinning speed is preferably 0.01 to 0.1 m/(m/min), and more preferably 0.01 to 0.05 m/(m/min). If the ratio of the air gap to the spinning speed is less than 0.01 m/(m/min), it is difficult to obtain a membrane having the structure and the performance of the present invention. If the ratio is more than 0.1 m/(m/min), a considerable amount of breaking occurs in the air gap due to high tension applied to the membrane, whereby production-unpreferably becomes difficult.

The spinning speed used herein means the winding speed when the stretch operation is not performed during a series of hollow fiber membrane production process in which the membrane-forming solution discharged from the nozzle together with the internal solution passes through the air gap and the membrane coagulated in the coagulation bath is wound. A hollow fiber membrane can be more stably produced by enclosing the air gap with a cylinder or the like and causing gas having a constant temperature and humidity to flow through the air gap at a specific flow rate.

As to the coagulation bath, a liquid in which the polymer is not dissolved, such as water; alcohols such as methanol and ethanol; ethers; aliphatic hydrocarbons such as n(normal)-hexane and n-heptane; and the like may be used. Of these, water is preferable. It is possible to control the coagulation speed or the like by adding a solvent in which the polymer is dissolved in the coagulation bath in a small amount.

The temperature of the coagulation bath is preferably 90 to 100° C. If the temperature of the coagulation bath is less than 90° C., the protein permeability may be decreased when subjecting bovine plasma to inside-out filtration. If the temperature of the coagulation bath is 100° C. or more, unpreferably the membrane frequently breaks during membrane formation.

In order to obtain the membrane of the present invention, the ratio of the thickness to the internal diameter of the membrane after coagulation is 0.15 to 0.4, and preferably 0.2 to 0.3. If the ratio of the thickness to the internal diameter of the membrane is less than 0.15, the absolute strength of the membrane tends to be decreased. If the ratio exceeds 0.4, a membrane having a gradient structure in which the pore size is decreased from the outer surface to the inner surface (or inner surface region) of the membrane as in the present invention may not be obtained. This is because, since the ratio of the amount of solvent in the membrane-forming solution to the amount of non-solvent in the internal solution is large, phase separation from the inner surface region to the outer surface region of the membrane-forming solution cannot be completed using only the amount of the non-solvent in the internal solution before immersion in the coagulation bath.

The external diameter of the membrane is 400 μm or less, and preferably 300 μm or less. Given that the membrane area (filling amount) in the module must be reduced as the external diameter of the membrane is increased, as a result, the treatment performance per unit time is unpreferably decreased. On the other hand, the size of the module container/vessel must be enlarged in order to maintain the membrane area (filling amount) in the module while increasing the external diameter of the membrane, whereby the cost is unpreferably increased. Given that the membrane of the present invention is used for medical applications, it is necessary to avoid providing an expensive and large-scale module in order to reduce the burden on the patients relating to medical expenses. Therefore, the external diameter of the membrane is preferably 400 μm or less due to the above-described relationship between the performance and cost.

The membrane of the present invention may be dried. The membrane may be or may not be impregnated with a moisture retention agent such as glycerol when drying the membrane.

The amount of elution from the membrane can be reduced since a part of PVP in the membrane may be water-insoluble by applying radiation such as electron beams or γ-rays to the membrane. The radiation may be applied before or after assembling the module.

The amount of water-insoluble PVP used in the present invention indicates the amount of PVP obtained by subtracting the amount of water-soluble PVP from the total amount of PVP in the membrane. The total amount of PVP in the membrane may be easily calculated by elemental analysis of nitrogen and sulfur.

The amount of water-soluble PVP may be determined by the following method.

In the case where the hydrophobic polymer is the polysulfone polymer, the membrane is completely dissolved in N-methyl-2-pyrrolidone, and water is added to the resulting polymer solution to cause the hydrophobic polymer to precipitate completely. The amount of water-soluble PVP may be determined by allowing the polymer solution to stand and determining the amount of PVP in the supernatant liquid by liquid chromatography.

Figure 4:
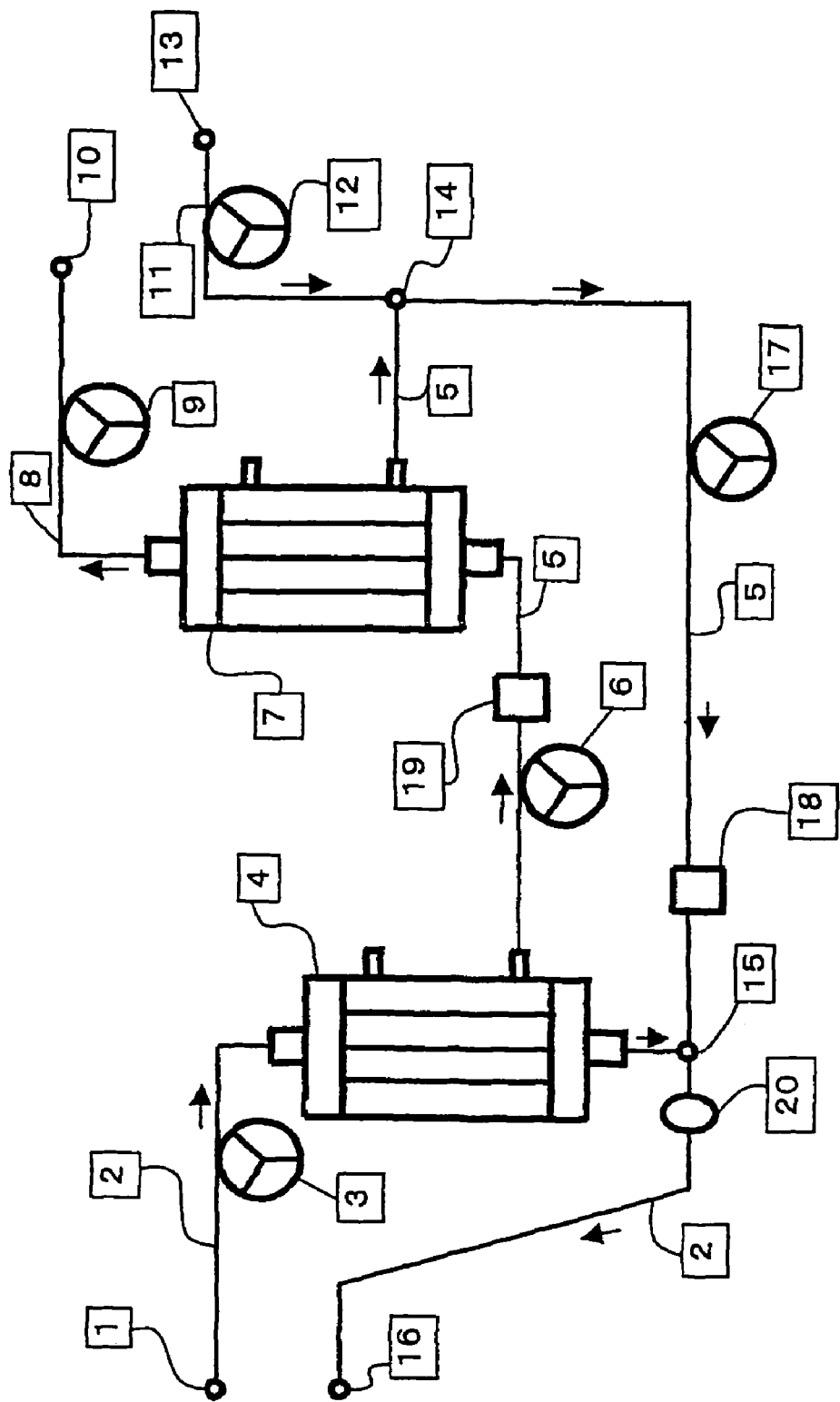
FIG. 4 is an elevation view of an example of a plasma purification system of the present invention.

An example of the plasma purification system of the present invention is described below with reference to the drawing. In FIG. 4, blood supplied from a blood inlet (1) to a blood circuit (2) is fed to a plasma separator (4) under pressure by a blood pump (3). The conditions are sufficiently adjusted before introducing the blood into the system by introducing a replenishment solution such as a physiological saline solution into the entire system. Bubbles can be removed from the system by this condition adjustment.

The plasma separator has a function of separating the blood into the blood cell components and the plasma components. As to the plasma separator, commercially available filter membrane separators and centrifugal separators such as Plasmaflow (manufactured by Asahi Medical Co., Ltd.), Plasmacure (manufactured by Kuraray Co., Ltd.), Sulflux (manufactured by Kaneka Corporation), and Propylex (made by Ube Industries, Ltd.) can be used. However, the present invention is not limited thereto.

The plasma separated by the plasma separator passes through a plasma circuit (5) by a plasma supply pump (6), and is introduced into a plasma component separator (7).

The plasma is separated into the discharge-liquid including pathogenic substances and the plasma components from which the pathogenic substances are removed or reduced by the plasma component separator (7) The discharge liquid is discharged from a discharge outlet (10) through a discharge tube (8) by a discharge pump (9).

The plasma from which the pathogenic substances are removed or reduced is supplied to a first mixing means (14) for mixing the plasma components with the replenishment solution. The replenishment solution is introduced through a replenishment solution inlet (13), and is supplied to the first mixing means (14) through a replenishment solution introduction tube (11) by a replenishment solution pump (12). As to the first mixing means (14) for mixing the plasma components with the replenishment solution, a tube connector or the like is used. Introduction of the replenishment solution into the system and discharge of the discharge liquid from the system may be performed continuously or intermittently. As to the replenishment solution, fresh frozen plasma, an albumin product, a physiological saline solution, or the like is used.

The plasma components supplied to the first mixing means (14) are mixed with the replenishment solution, and supplied to the second mixing means (15) in order to mix with the blood cell components separated by the plasma separator (4) using a plasma recovery pump (17). As to the second mixing means for mixing the blood cell components with the plasma components, a venous chamber or the like can be used; Blood into which the plasma, from which the pathogenic substances are removed or reduced, and the blood cell components are mixed in the second mixing means, and which is made the original blood state is recovered through a blood outlet 16).

A disease can be improved by removing the pathogenic substances from the blood by repeating the above-described steps. The blood inlet (1) and the blood outlet (16) may be directly connected with the living body, whereby a treatment can be continuously performed for a long period of time.

It is preferable to heat the plasma components upstream of the second mixing means (15)-using a means for heating plasma (18). If the temperature of the plasma components is too low, unpreferably the plasma components can not be uniformly mixed with the blood cell components, or the plasma components may not be directly returned to the living body from the blood outlet (16). As to the means for heating plasma (18), means for directly or indirectly heating the plasma using a heater and/or warm water can be exemplified.

Since the removal efficiency of the pathogenic substances separated by the plasma component separator (7) may change to a large extent depending on the temperature, the plasma introduced into the plasma component separator may be maintained at a desired temperature using a plasma component heating or cooling means (19). In the case where the plasma component heating or cooling means cannot be disposed upstream of the plasma component separator due to the circuit arrangement, it is possible to heat or cool the plasma component separator directly. As to the heating/cooling means, means for directly or indirectly contacting cooling water, a cooler, or the like with the plasma component separator during cooling, or means for directly or indirectly contacting warm water, a heater, or the like with the plasma component separator during heating can be used. The temperature is preferably in the range from 0 to 42° C.

In the case of directly returning the blood to the living body from the blood outlet (16), it is necessary to always monitor the blood using means for detecting bubbles in the blood (20) so that bubbles do not enter the blood returned. As to the means for detecting bubbles in the blood, a bubble detector can be used.

In order to cause the concentration (blood cell concentration) of the blood introduced into the system to be equal to the concentration (blood cell concentration) of the blood returned from the system after removing the pathogenic substances, it is preferable that the amount of discharge liquid from the plasma component separator be equal to the amount of replenishment solution. In order to cause the amount of discharge liquid to be equal to the amount of replenishment solution, the discharge pump (9) and the replenishment solution pump (12) may be controlled. However, since the balance between the amount of discharge liquid and the amount of replenishment solution may change depending on the change with time in the pressure distribution over the entire system, it is preferable to control the pumps and the like of the entire system using a computer. In order to cause the concentration (blood cell concentration) of the blood introduced into the system to be equal to the concentration (blood cell concentration) of the blood returned from the system, each pump and each mixing means may be controlled so that the amount of plasma supplied from the plasma separator to the plasma component separator is equal to the amount of plasma returned to the second mixing means.

A tube for blood such as a vinyl chloride tube is used as the blood circuit, the plasma circuit, and various inlet and outlet tubes. A valve, a clamp, or the like may be used in combination with such a tube.

The pathogenic substances in the present invention differ depending on the type of disease. Therefore, the present invention may be applied to, but not limited to, the following diseases. In the case where the disease is age-related macular degeneration, pathogenic substances such as fibrinogen (Fbg) and immunoglobulin (IgM) must be removed from blood (plasma). Similarly, in the case where the disease is multiple myeloma, M protein must be removed as pathogenic substances. In the case where the disease is primary macroglobulinemia, γ-globulin (IgG) must be removed. In the case where the disease is myasthenia gravis, an anti-acetyl receptor antibody must be removed. In the case where the disease is malignant rheumatoid arthritis, a rheumatoid factor and immune complex must be removed. In the case where the disease is hyperlipemia, LDL cholesterol must be removed. In the case where the disease is a severe blood type incompatible with pregnancy, Rh blood type incompatible sensitizing antibody must be removed. In the case where the disease is Guillain-Barre syndrome, a demyelinating factor and antibody must be removed. In the case where the disease is pemphigus, anti-epidermal cell membrane antibody and IgQ must be removed. In the case where the disease is bullous pemphigoid, an anti-basement membrane antibody and IgG must be removed. In the case where the disease is arteriosclerosis obliterans, LDL cholesterol must be removed. In the case where the disease is focal glomerular sclerosis, LDL cholesterol, IgG, and $C_3$ must be removed. In the case where the disease is allogeneic renal transplantation, an anti-ABO antibody and lymphocyte antibody must be removed. The present invention can be also applicable to viral diseases. In this case, the pathogenic substances are viruses. For example, diseases such as hepatitis B, HIV, and viral leukemia can be given. However, the present invention is not limited to these viral diseases.

BEST MODE FOR CARRYING OUT THE INVENTION

The present invention is described below by way of examples. However, the present invention is not limited to the following examples.

The measurement methods are as follows.

A hollow fiber membrane used as the measurement specimen was used in a dried state.

(Measurement of Water Permeation Amount)

Pure water (25° C.) was caused to permeate from the inner surface to the outer surface of a fiber bundle (mini module in which the number of membranes was adjusted so that the inner surface area was 110±10 cm$^2$) with an effective length of 180 mm of which both ends were secured using an adhesive, and the amount of pure water permeated was indicated in unit of mL/(m$^2$·hr·mmHg).

The effective membrane area was converted to the inner surface area.

(Measurement of Breaking Stress)

The membrane stress was measured under the condition of a specimen length of 20 mm and a tensile speed of 300 mm/min using an autograph AGS-5D manufactured by Shimadzu Corporation.

(Bovine Plasma Evaluation)

Bovine plasma (37° C.) was supplied at 0.5 mL/min to one end of the hollow section (inner surface side) of a fiber bundle (mini module) with an effective length of 180 mm of which both ends were secured using an adhesive, and was discharged from the other end of the hollow section at 0.1 mL/min. This cross-flow filtration of one-pass operation was performed for 180 min. The membrane area of the fiber bundle was adjusted by adjusting the number of membranes so that the linear velocity was 1 cm/min for the amount of bovine plasma supplied at 0.5 mL/min. The entire filtrate obtained by 180 min of filtration was homogeneously stirred. The membrane performance was evaluated by determining the concentration of each protein in the solution and the plasma before filtration. The permeability is a value represented by the following equation (6).

$$\text{Permeability (\%)} = (\text{concentration in filtrate})/(\text{concentration in original solution}) \times 100 \qquad (6)$$

(Measurement of Total Amount of Protein)

The total amount (concentration) of protein in the plasma (original solution) or the filtrate from the membrane was measured at a wavelength of 540 nm using a spectrophotometer after mixing 5 mL of a total protein coloring reagent (manufactured by Wako Pure Chemical Industries, Ltd.) with 0.1 mL of the solution (plasma (original solution) or filtrate from the membrane) and allowing the mixture to stand for 30 min.

(Measurement of Immunoglobulin (IgM) Concentration)

The concentration of immunoglobulin (IgM) in the plasma (original solution) or the filtrate from the membrane was measured using a Behring Nephelometer Analyzer BM (manufactured by Dade Behring Inc.).

EXAMPLE 1

(Membrane Formation and Removal of Residual Solvent)

20.0 wt % of polysulfone ("P-1700" manufactured by Amoco Engineering Polymers of the U.S.) and 6.0 wt % of polyvinylpyrrolidone ("K90" manufactured by BASF of Germany, weight average molecular weight: 1,200,000) were dissolved in 74.0 wt % of N-methyl-2-pyrrolidone to obtain a homogenous solution. The mixing ratio of polyvinylpyrrolidone to polysulfone in the membrane-forming solution was 30.0 wt %. The membrane-forming solution was maintained at 60° C., and discharged from a spinning nozzle (double annular nozzle, 0.1 mm-0.2 mm-0.3 mm, nozzle temperature: 60° C., temperature of membrane-forming solution at nozzle: 60° C.) together with an internal solution consisting of a mixed solution of 46 wt % of N-methyl-2-pyrrolidone and 54 wt % of water. The discharged mixture was caused to pass through an air gap having a length of 0.96 m, and was immersed in a coagulation bath containing water at 95±1° C.

The section from the spinning nozzle to the coagulation bath was enclosed using a cylindrical tube for a seal so that the outside air did not enter therein. The spinning speed was fixed at 80 m/min. The ratio of the air gap to the spinning speed was 0.012 m/(m/min).

The wound fiber bundle was cut, and was washed for two hours by showering hot water at 80° C. on the cut surface of the bundle to remove the residual solvent from the membrane. The membrane was dried for seven hours using hot blast at 87° C. to obtain a dried membrane having a water content of less than 1%. A part of PVP in the membrane was insolubilized by applying γ-rays to the dried membrane at 2.5 Mrad.

(Evaluation of Membrane Structure and Membrane Performance)

The resulting membrane was observed using an electron microscope, and it was found that the membrane had a sponge structure in which the pore size was continuously decreased from the outer surface to the inner surface of the membrane. FIGS. 1 to 3 show electron micrographs of the membrane obtained in this example. The membrane structure, the membrane performance, and the like are shown in Table 1. The membrane exhibited a high breaking stress of 50 kgf/cm$^2$ or more, and had a total protein permeability of 50% or more when subjecting bovine plasma to inside-out filtration. The membrane maintained a stable filtration amount for a long period of time without occurrence of rapid clogging during the inside-out filtration of bovine plasma.

EXAMPLE 2

The same operation as in Example 1 was performed except for using an internal solution consisting of a mixed solution of 54 wt % of N-methyl-2-pyrrolidone and 46 wt % of water (water content: 46 wt %). The resulting membrane was observed using an electron microscope, and it was found that the membrane had a sponge structure in which the pore size was continuously decreased from the outer surface to the inner surface of the membrane. The membrane structure and the membrane performance are shown in Table 1. The membrane exhibited a high breaking stress of 50 kgf/cm$^2$ or more, and had a total protein permeability of 50% or more when subjecting bovine plasma to inside-out filtration. The membrane maintained a stable filtration amount for a long period of time without occurrence of rapid clogging during the inside-out filtration of bovine plasma.

EXAMPLE 3

The same operation as in Example 1 was performed except for using an internal solution consisting of a mixed solution of 58 wt % of N-methyl-2-pyrrolidone and 42 wt % of water (water content: 42 wt %). The resulting membrane was observed using an electron microscope, and it was found that the membrane had a sponge structure in which the pore size was continuously decreased from the outer surface to the inner surface of the membrane. The membrane structure and the membrane performance are shown in Table 1. The membrane exhibited a high breaking stress of 50 kgf/cm$^2$ or more, and had a total protein permeability of 50% or more when subjecting bovine plasma to inside-out filtration. The membrane maintained a stable filtration amount for a long period of time without occurrence of rapid clogging during the inside-out filtration of bovine plasma.

EXAMPLE 4

The same operation as in Example 1 was performed except for changing the amounts of polyvinylpyrrolidone and N-methyl-2-pyrrolidone in the membrane-forming solution to 10.0 wt % and 70 wt %, respectively. The mixing ratio of polyvinylpyrrolidone to polysulfone in the membrane-forming solution was 50.0 wt %. The resulting membrane was observed using an electron microscope, and it was found that the membrane had a sponge structure in which the pore size was continuously decreased from the outer surface to the inner surface of the membrane. The membrane structure and the membrane performance are shown in Table 1. The membrane exhibited a high breaking stress of 50 kgf/cm$^2$ or more, and had a total protein permeability of 50% or more when subjecting bovine plasma to inside-out filtration. The membrane maintained a stable filtration amount for a long period of time without occurrence of rapid clogging during the inside-out filtration of bovine plasma.

EXAMPLE 5

The same operation as in Example 1 was performed except for using the membrane-forming solution having 8.0 wt % of polyvinylpyrrolidone and 70 wt % of N-methyl-2-pyrrolidone. The mixing ratio of polyvinylpyrrolidone to polysulfone in the membrane-forming solution was 40.0 wt %. The resulting membrane was observed using an electron microscope, and it was found that the membrane had a sponge structure in which the pore size was continuously decreased from the outer surface to the inner surface of the membrane. The membrane structure and the membrane performance are shown in Table 1. The membrane exhibited a high breaking stress of 50 kgf/cm$^2$ or more, and had a total protein permeability of 50% or more when subjecting bovine plasma to inside-out filtration. The membrane maintained a stable filtration amount for a long period of time without occurrence of rapid clogging during the inside-out filtration of bovine plasma.

COMPARATIVE EXAMPLE 1

The same operation as in Example 1 was performed except for using an internal solution consisting of a mixed solution of 43 wt % of N-methyl-2-pyrrolidone and 57 wt % of water (water content: 57 wt %). The resulting membrane was observed using an electron microscope, and it was found that the membrane had a sponge structure in which the pore size was continuously decreased from the outer surface to the inner surface of the membrane. The membrane structure and the membrane performance are shown in Table 2. The membrane had a total protein permeability of less than 50% when subjecting bovine plasma to inside-out filtration.

COMPARATIVE EXAMPLE 2

The same operation as in Example 1 was performed except for using an internal solution consisting of a mixed solution of 62 wt % of N-methyl-2-pyrrolidone and 38 wt % of water (water content: 38 wt %). However, a membrane could not be spun due to occurrence of frequent breaking.

COMPARATIVE EXAMPLE 3

The same operation as in Example 1 was performed except for changing the amounts of polyvinylpyrrolidone and N-methyl-2-pyrrolidone in the membrane-forming solution to 5.0 wt % and 75.0 wt %, respectively. The mixing ratio of polyvinylpyrrolidone to polysulfone in the membrane-forming solution was 25.0 wt %. The resulting membrane was observed using an electron microscope, and it was found that the membrane had a sponge structure in which the pore size was continuously decreased from the outer surface to the inner surface of the membrane. The membrane structure and the membrane performance are shown in Table 2. The membrane had a total protein permeability of less than 50% when subjecting bovine plasma to inside-out filtration.

COMPARATIVE EXAMPLE 4

20 wt % of polysulfone, 13 wt % of polyvinylpyrrolidone, and 67 wt % of N-methyl-2-pyrrolidone used in Example 1 were mixed. However, a homogenous solution could not be obtained.

COMPARATIVE EXAMPLE 5

The same operation as in Example 2 was performed except for changing the temperature of the membrane-forming solution to 45° C. and the nozzle temperature to 45° C. (temperature of membrane-forming solution at nozzle: 45° C.) However, a membrane could not be spun due to occurrence of frequent breaking.

COMPARATIVE EXAMPLE 6

The same operation as in Example 1 was performed except for changing the solvent from N-methyl-2-pyrrolidone to N,N-dimethylacetamide. The resulting membrane was observed an electron microscope, and it was found that the membrane had a sponge structure in which the pore size was continuously decreased from the outer surface to the inner surface of the membrane. The membrane structure and the membrane performance are shown in Table 2. The membrane had a total protein permeability of less than 50% when subjecting bovine plasma to inside-out filtration.

COMPARATIVE EXAMPLE 7

The same operation as in Comparative Example 6 was performed except for using a mixed solution of 95-wt % of N,N-dimethylacetamide and 5 wt % of water as the internal solution. The resulting membrane was observed using an electron microscope, and it was found that the membrane had a sponge structure in which the pore size was continuously decreased from the inner surface to the outer surface of the membrane. The membrane structure and the membrane performance are shown in Table 2. Since a rapid increase in pressure (clogging) occurred when 35 min had elapsed after subjecting bovine plasma to inside-out filtration, the evaluation was terminated.

COMPARATIVE EXAMPLE 8

The bovine plasma evaluation was performed in the same manner as disclosed in Example 1 except for using a hollow fiber membrane with an internal diameter of 200 μm and a thickness of 46 μm obtained by using the method disclosed in Example 1 of Japanese Patent Application Laid-open No. 58-155865. Since an increase in pressure (clogging) occurred when 120 min had elapsed after subjecting bovine plasma to inside-out filtration, the evaluation was terminated.

TABLE 1

| | Example | | | | |
| --- | --- | --- | --- | --- | --- |
| | 1 | 2 | 3 | 4 | 5 |
| Internal diameter (μm) | 210 | 216 | 208 | 212 | 194 |
| External diameter (μm) | 300 | 308 | 304 | 306 | 278 |
| Thickness (μm) | 45 | 46 | 48 | 47 | 42 |
| Ratio of thickness to internal diameter | 0.214 | 0.213 | 0.231 | 0.222 | 0.216 |
| Amount of water permeation (mL/(m$^2$ · hr · mmHg)) | 1310 | 1600 | 3600 | 1050 | 1440 |
| Average pore size on outer surface (μm) | 1.2 | 1.2 | 2.0 | 1.1 | 1.1 |
| Porosity of outer surface (%) | 15.1 | 15.5 | 15.3 | 17.1 | 16.2 |
| Breaking stress (kgf/cm$^2$) | 75 | 74 | 71 | 77 | 76 |

TABLE 1-continued

|  | Example | | | | |
| --- | --- | --- | --- | --- | --- |
|  | 1 | 2 | 3 | 4 | 5 |
| PVP concentration on inner surface (wt %) | 36 | 36 | 33 | 35 | 34 |
| Total protein permeability (%) | 64 | 90 | 99 | 57 | 66 |
| Immunoglobulin (IgM) permeability (%) | 23 | 56 | 87 | 18 | 25 |
| Presence or absence of water-insoluble PVP | Present | Present | Present | Present | Present |

TABLE 2

|  | Comparative Example | | | |
| --- | --- | --- | --- | --- |
|  | 1 | 3 | 6 | 7 |
| Internal diameter (μm) | 190 | 216 | 216 | 201 |
| External diameter (μm) | 272 | 304 | 304 | 291 |
| Thickness (μm) | 41 | 44 | 44 | 45 |
| Ratio of thickness to internal diameter | 0.216 | 0.204 | 0.204 | 0.224 |
| Amount of water permeation (mL/(m² · hr · mmHg)) | 760 | 410 | 410 | 2850 |
| Average pore size on outer surface (μm) | 1.1 | 1.0 | 1.0 | 0.03 |
| Porosity of outer surface (%) | 14.9 | 16.0 | 16.0 | 13.2 |
| Breaking stress (kgf/cm²) | 75 | 58 | 58 | 42 |
| PVP concentration on inner surface (wt %) | 31 | 34 | 34 | 5 |
| Total protein permeability (%) | 47 | 21 | 21 | — |
| Immunoglobulin (IgM) permeability (%) | 1 | 0 | 0 | — |
| Presence or absence of water-insoluble PVP | Present | Present | Present | Present |

EXAMPLE 6

11,400 membranes of Example 1 were bundled and secured at both ends to a cylindrical housing using a polyurethane resin to form a module with an effective membrane area of 2 m². The resulting module was used as a plasma component separator. A system similar to the system shown in FIG. 4 was formed using Plasmaflow (manufactured by Asahi Medical Co., Ltd.; membrane area: 0.8 m²) as a plasma separator, and human blood was treated using the system for three hours.

The treatment conditions were as follows.

Amount of blood supplied to plasma separator: 70 mL/min, amount of plasma component supplied from plasma separator to plasma component separator: 20 mL/min, amount of discharge liquid: 5 mL/min, amount of replenishment solution supplied: 5 mL/min, temperature of means for heating plasma (18): 37° C., temperature of means for heating or cooling plasma (19): 25° C., and replenishment solution: albumin product.

The blood of a patient suffering from age-related macular degeneration was used as the objective blood, and the system was directly connected with the human body.

The above treatment was performed four times at intervals of 10 days. As a result, alteration in visual acuity decreased with time ceased after the second treatment, and improvement of vision was recognized after the fourth treatment. The values of fibrinogen and immunoglobulin in the blood before the treatment were 320 mg/dL and 120 mg/dL, respectively. These values were clearly reduced to 140 mg/dL and 40 mg/dL respectively after the treatment.

EXAMPLE 7

The blood of a patient suffering from hyperlipidemia was treated for 200 min by using the same method as in Example 6. The treatment conditions were as follows. Amount of blood supplied to plasma separator: 100 mL/min, amount of plasma component supplied from plasma separator to plasma component separator: 40 mL/min, amount of discharge liquid: 5 mL/min, amount of replenishment solution supplied: 5 mL/min, temperature of means for heating plasma (18): 37° C., temperature of means for heating or cooling plasma (19): 20° C., and replenishment solution: albumin preparation. The treatment was performed twice at an interval of one week. As a result, the total cholesterol value in the blood, which was 560 mg/dL before the treatment, was reduced to 190 mg/dL after the treatment.

INDUSTRIAL APPLICABILITY

According to the present invention, an excellent plasma purification membrane which rarely clogs, and has high strength during plasma purification using inside-out filtration, and an excellent blood purification system were obtained. Therefore, the present invention can be used for drug applications, medical applications, and general industrial applications.

The invention claimed is:

1. A hollow fiber plasma purification membrane, comprising:
   an aromatic polysulfone and polyvinylpyrrolidone and having a polyvinylpyrrolidone concentration on an inner surface of the membrane of 20 to 40 wt%, the membrane having a sponge structure in which a pore size is continuously decreased from an outer surface to the inner surface of the membrane, and having a breaking stress of 71 kgf/cm² or more, and when subjecting bovine plasma to inside-out filtration the membrane having a total protein permeability of 50% or more and an immunoglobulin (IgM) permeability of 90% or less when subjecting bovine plasma to inside-out filtration.

2. The hollow fiber plasma purification membrane according to claim 1, wherein the membrane has circular or elliptical pores having an average pore size of 1 μm or more on the outer surface of the membrane.

3. The hollow fiber plasma purification membrane according to claim 1, wherein porosity of the outer surface of the membrane is 10% or more.

4. The hollow fiber plasma purification membrane according to claim 1, wherein the membrane has a ratio of thickness to internal diameter of 0.15 to 0.4.

5. The hollow fiber plasma purification membrane according to claim 1, wherein the membrane has an external diameter of 400 μm or less.

6. The hollow fiber plasma purification membrane according to claim 1, wherein the polyvinylpyrrolidone has a weight average molecular weight of 900,000 or more.

7. The hollow fiber plasma purification membrane according to claim 1, wherein the membrane comprises water-insoluble polyvinylpyrrolidone.

8. The hollow fiber plasma purification membrane according to claim 1, wherein the membrane is used to treat a patient suffering from age-related macular degeneration.

9. The hollow fiber plasma purification membrane according to claim 1, wherein the membrane is used to treat a patient suffering from hyperlipidemia.

10. A plasma purification system, comprising: a plasma separator including a separation membrane which separates blood into blood cell components and plasma components; a plasma component separator including a separation membrane which separates the separated plasma components into pathogenic substances and plasma components from which the pathogenic substances are removed or reduced; first mixing means for mixing the plasma components from which the pathogenic substances are removed or reduced with a replenishment solution; and second mixing means for further mixing the plasma components subjected to the first mixing means with the blood cell components separated by the plasma separator; wherein the separation membrane included in the plasma component separator is the membrane according to claim 1.

11. The plasma purification system according to claim 10, further comprising means for heating plasma upstream of the second mixing means for mixing the plasma components with the blood cell components.

12. The plasma purification system according to claim 10, comprising means for heating or cooling plasma downstream of the plasma separator and upstream of the plasma component separator.

13. The plasma purification system according to claim 10, wherein an amount of discharge liquid including the pathogenic substances discharged from the plasma component separator is equal to an amount of the replenishment solution.

14. The plasma purification system according to claim 10, which is controlled so that an amount of the plasma supplied from the plasma separator to the plasma component separator is equal to an amount of the plasma returned to the second mixing means.

15. The plasma purification system according to claim 10, further comprising means for detecting bubbles in the blood downstream of the second mixing means and upstream of a blood outlet.

16. A plasma purification method comprising using the plasma purification system of claim 10 for treating blood, the process comprising the steps of:
   subjecting the blood with a separation membrane which separates the blood into cell components and plasma components;
   subjecting the plasma component with a membrane that separates or reduces pathogenic substances from plasma;
   mixing the plasma from which the pathogenic substances are remove or reduced with a replenishing solution; and
   further mixing the mixture of plasma and replenishing solution with the blood cells components separated by the plasma separator.

17. The method of claim 16, wherein said method treats a decease from blood of a leaving body.

18. The method of claim 16, wherein the method is used for treating a patient suffering from age-related macular degeneration.

19. The method of claim 16, wherein the method is used for treating a patient suffering from hyperlipidemia.

20. A method for producing a hollow fiber plasma purification membrane comprising a hydrophobic polymer and a hydrophilic polymer, having a sponge structure in which a pore size is continuously decreased from an outer surface to an inner surface of the membrane, and having a breaking stress of 71 kgf/cm$^2$ or more, and a total protein permeability of 50% or more and an immunoglobulin (IgM) permeability of 90% or less when subjecting bovine plasma to inside-out filtration, comprising the steps of: discharging a membrane-forming solution and an internal solution from a double annular nozzle, passing the discharged mixture through an air gap, and coagulating the resulting mixture in a coagulation bath;
   the method further characterized in that:
   a) the membrane-forming solution comprises a hydrophobic polymer, a solvent for the hydrophobic polymer, and a hydrophilic polymer, and has a ratio of the hydrophilic polymer to the hydrophobic polymer of 27 to 60 wt %;
   b) the internal solution comprises water and at least one solvent, and has a water content of 40 to 55 wt%;
   c) the membrane-forming solution has a temperature of 50° C. or more at the nozzle;
   d) the coagulation bath has a temperature of 90 to 100° C.; and
   e) a ratio of the air gap to spinning speed is 0.01 to 0.1 m/(m/min).

21. The method for producing a hollow fiber plasma purification membrane according to claim 20, further comprising the step of applying radiation to the membrane.

22. The method for producing a hollow fiber plasma purification membrane according to claim 20, wherein the hydrophobic polymer is a polysulfone polymer.

23. The method for producing a hollow fiber plasma purification membrane according to claim 20, wherein the solvent for the hydrophobic polymer is N-methyl-2-pyrrolidone.

24. The method for producing a hollow fiber plasma purification membrane according to claim 20, wherein the spinning speed is 60 m/min or more.

* * * * *